United States Patent
Davis

[11] Patent Number: 6,131,576
[45] Date of Patent: Oct. 17, 2000

[54] MALE INCONTINENCE CLAMP, KIT AND METHOD OF USE

[76] Inventor: Paul K. Davis, 4040 Eagles Nest, Auburn, Calif. 95604

[21] Appl. No.: 09/207,380

[22] Filed: Dec. 8, 1998

Related U.S. Application Data

[63] Continuation-in-part of application No. 09/046,244, Mar. 23, 1998, abandoned.

[51] Int. Cl.[7] ........................................... A61F 5/48
[52] U.S. Cl. .................................. 128/885; 128/DIG. 25; 600/29
[58] Field of Search ..................... 128/869, 885, 128/886, DIG. 25; 60/29–31

[56] References Cited

U.S. PATENT DOCUMENTS

| | | |
|---|---|---|
| 714,850 | 12/1902 | Zimmermann . |
| 1,728,322 | 9/1929 | Badrian ........................ 128/DIG. 25 |
| 3,147,754 | 9/1964 | Koessler . |
| 3,203,421 | 8/1965 | Bialick . |
| 5,415,179 | 5/1995 | Mendoza . |
| 5,571,125 | 11/1996 | Chadwick ........................ 128/DIG. 25 |

*Primary Examiner*—Michael A. Brown
*Attorney, Agent, or Firm*—Philip A. Dalton

[57] ABSTRACT

A clamp is disclosed, which prevents penile leakage. The clamp includes a generally convex lower bow; a generally concave upper bow; and a hinge which pivotally joins the bows at one end. A releasable, preferably removable latch at the opposite end is used to hold the bows closed about the penis. When the clamp is closed, the bows form an enclosure having center and side regions which together approximate the area of the uncompressed penis. The bows are spaced apart a small distance at approximately their center, for compressively closing the urethra. The musculus expands into the side regions of the enclosure to permit blood circulation to the head. One or both of the bows may be a one-piece member of rigid, yet flexible material. Preferably, the hinge and latch are adjustable, to provide spacing between the bows and adjustable compression of the penis. Alternatively, one or both of the bows may comprise a frame member and a tubular cover. A clamp kit includes a plurality of removable latches of different lengths, to provide different spacings between the bows.

4 Claims, 5 Drawing Sheets

MALE INCONTINENCE CLAMP, KIT AND METHOD OF USE

This is a continuation-in-part of U.S. application Ser. No. 09/046,244 entitled MALE INCONTINENCE CLAMP, KIT AND METHOD OF USE, filed Mar. 23, 1998 now abandoned, in the name of inventor Paul K. Davis.

BACKGROUND OF THE INVENTION

Field of the Invention

The present invention relates generally to devices for controlling male urinary leakage.

Definitions and Applicability

Typically, as used here, "urinary leakage" and "incontinence" are used interchangeably. For convenience, in describing the clamp embodying the present invention, reference is made to "upper" and "lower" bow members, however it is understood that this orientation is illustrative and not limiting to any particular orientation or position. For example, the bows could be positioned "left" and "right" or vice versa, or at any of many other orientations which allow the necessary clamping.

Current State of the Relevant Field

Many males experience problems with the physiological function of urinary control which result in urinary leakage. The problems may be the result of disease or of the aging process. Also, radical surgery, radiation or chemotherapy to remove or treat a cancerous prostate gland has a high probability of causing some degree of long term urinary incontinence. There is a need for a device which effectively prevents urinary leakage, can be worn with very little discomfort for extended periods of time, and is quickly opened when there is an urge to urinate and quickly closed when the bladder is empty. Furthermore, preferably such a device should be easily adjusted to a wide range of sizes.

SUMMARY OF THE INVENTION

In one embodiment, the present invention is embodied in a clamp, adapted for stopping penile leakage, comprising a lower bow having first and second ends; an upper bow having first and second ends; a pivot or hinge pivotally joining the bows at the first ends; and a releasable latch for holding the closed bows together at the second ends. The configuration of the bows is such that, when the clamp is closed, the bows define an enclosure having a center region and side regions. The bows are closely spaced in the center region for compressing the lumen of urethra. The side regions receive the musculus displaced by the compression. The area of the enclosure is sufficiently large to maintain blood circulation.

In another embodiment, the present invention is embodied in a clamp, adapted for stopping penile leakage, comprising a generally convex lower bow having first and second ends; a generally concave upper bow having first and second ends; a hinge pivotally joining the bows at the first ends; and a releasable latch for holding the bows closed together at their second ends. When the clamp is closed, the bows form an enclosure having center and side regions which collectively are at least the area of an uncompressed penis. The bows of the closed clamp are spaced apart a first, relatively small distance at approximately their center, and thus compress the penis and close the lumen of urethra. The bows are spaced apart a second distance, preferably greater than the first distance on opposite sides of the center, allowing the penis to expand into the side regions of the enclosure to maintain blood circulation to the penis head.

In another aspect, one and preferably each of the upper and lower bows is a one-piece member of rigid, yet flexible material. In an alternative aspect, one or each of the bows comprises a frame member and a tubular cover.

The compression of the penis may be varied by using pivots or hinges of different lengths or adjustable lengths and/or by using latches of different lengths or adjustable lengths. Most preferably an adjustable length pivot or hinge and an adjustable length latch are used.

In a preferred aspect, the present invention is embodied in a clamp as described above, and wherein the hinge and latch comprise threaded eye studs at the first and second pivot points for altering the spacing between the closed bows and the resulting compression of the shaft of the penis clamped therebetween.

In yet another aspect, the present invention is embodied in a kit for a clamp as described above, and including a plurality of latches of different lengths for altering the spacing between the closed bows and the resulting compression of the shaft of a penis clamped therebetween.

In another, method aspect, the present invention is embodied in a method for stopping penile leakage, comprising applying a clamp to the penis for compressing a penis proximate the cross-sectional center thereof to close the lumen of urethra and suppress liquid flow through the lumen of urethra, while allowing sideways displacement of the musculus of the penis by the compression, to maintain blood circulation to the penis head.

In yet another, method aspect, the present invention is embodied in a method for stopping penile leakage, comprising providing a clamp having upper and lower bows, positioning the clamp transversely across the shaft of a penis, and closing the bows to a first spacing proximate the cross-sectional center of the penis shaft and to a second spacing on opposite sides of the penis shaft, the first spacing closing the lumen of urethra and suppressing liquid flow through the lumen of urethra, and the second spacing allowing sideways displacement of the penis to maintain blood circulation to the penis head.

Other aspects and embodiments of the present invention are described in the specification, drawings and claims.

BRIEF DESCRIPTION OF THE DRAWINGS

The above and other aspects of the invention are described below in conjunction with the following drawings.

DETAILED DESCRIPTION OF THE PREFERRED EMBODIMENT(S)

1. One-Piece Bow Embodiment a. Design and Construction

FIGS. 1–6 depict an embodiment 10 of a male incontinence clamp which embodies the present invention. The clamp 10 comprises a lower bow-shaped member or bow 11 and an upper bow-shaped member or bow 16 which are pivotally joined at one end by pivot or pivotal hinge assembly 20 and are secured at the opposite end by latch assembly 25. As explained in detail below, when the clamp is closed about the penis, the pivotal latch assembly 25 secures the lower bow 11 and upper bow 16 together, and the bows compress the penis in such a way that leakage is prevented, yet blood circulation is maintained to the clamped head end of the penis.

For convenience I refer to the lower bow as being convex and the upper bow as being concave. Referring to FIGS. 1–3 and 5–6, the two bows have mating, vertically short u-shaped configurations. Preferably each bow is a relatively rigid, yet resilient single piece member formed of material such as plastic. The lower bow 11 comprises an upward-extending (inward-extending) center section or projection 12 flanked by opposite side sections 13 and 14. Projection 12 has a slight depression at approximately its center, which helps in positioning and mounting the clamp 10 on the shaft of a penis. Projection 12 and mating side sections 13 and 14 on bow 11, have blended radii and are highly polished to prevent irritation when closed on the penis shaft. The upper bow 16 comprises an upward-extending (outward-extending) center section 17 flanked by opposite side sections 18 and 19. Projection 17 and mating side sections 18 and 19 on bow 16, have blended radii and are highly polished to prevent irritation when closed on the penis shaft.

The slotted end section pivotal hinge member 21 of hinge assembly 20 is formed at one end of one of the bows, illustratively the left end of the lower bow 11. Preferably, the bifurcated, u-shaped hinge member 21 comprises extensions defining a slotted opening for receiving slotted or hook-shaped end section or member 22 formed in a corresponding first end of the other bow, illustratively the left end of bow 16. Pivot pin 23 is mounted in holes in the extensions of hinge member 21, preferably in a removable, friction fit. Pivot pin 23 receives hook 22 of bow 16, providing a pivotal attachment point for lower bow 11 and upper bow 16. Preferably, the hook 22 provides a secure but releasable friction fit over pin 23. Illustratively, the pin-receiving opening of the hook 22 faces upward when the clamp is closed, FIGS. 3 and 6, and downward or outward when the clamp is open, FIGS. 1 and 2. Thus, the hook 22 on upper bow 16 is secured to the pin 23 in lower bow when the clamp is closed, but is easily removed from the pin when the clamp is open, for cleaning, repair, replacement, etc. Also, pin 23 can be mounted in hinge member 21 via a removable friction fit.

Figures 1, 2, 3:
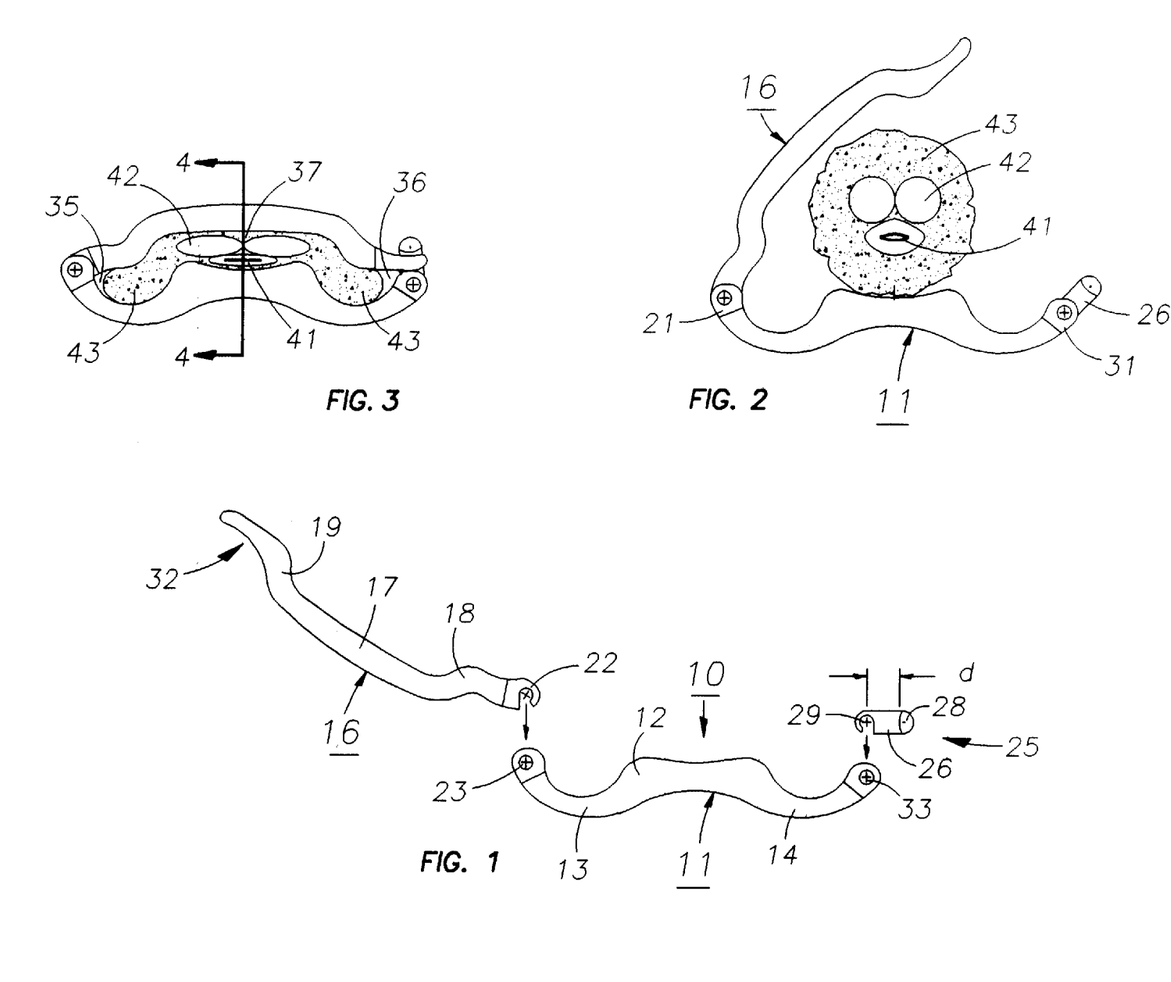
FIG. 1 is an exploded front elevation view depicting one embodiment of a clamp in accordance with the present invention.
FIG. 2 depicts a transverse cross-sectional view of a penis about which the clamp of FIG. 1 is horizontally centered in an open orientation, prior to closure.
FIG. 3 is a transverse cross-sectional view of a penis showing the clamp of FIG. 1 closed or clamped and illustrating the compression by the closed clamp.
Figure 5:
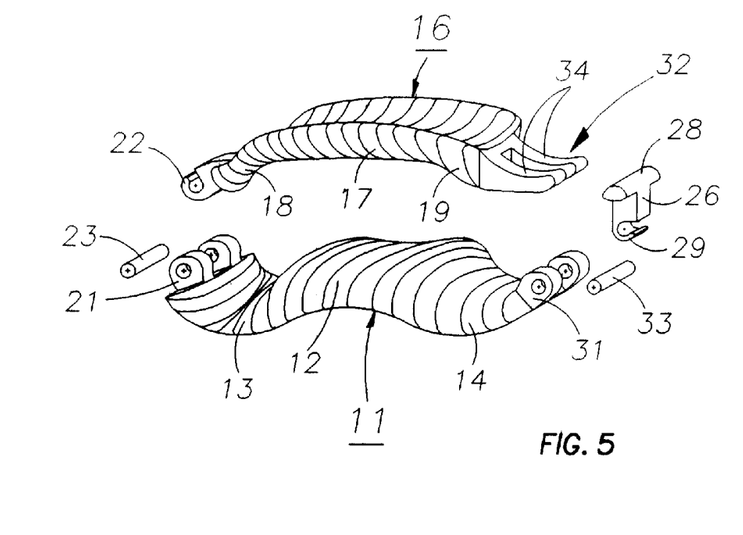
FIG. 5 is an isometric exploded view of the parts forming the clamp assembly shown in FIGS. 1–4.
Figure 6:
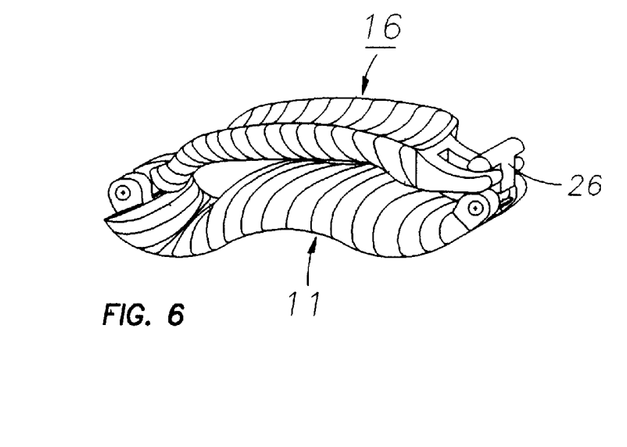
FIG. 6 is an isometric view of the clamp assembly shown in FIG. 3.
Figures 7, 8:
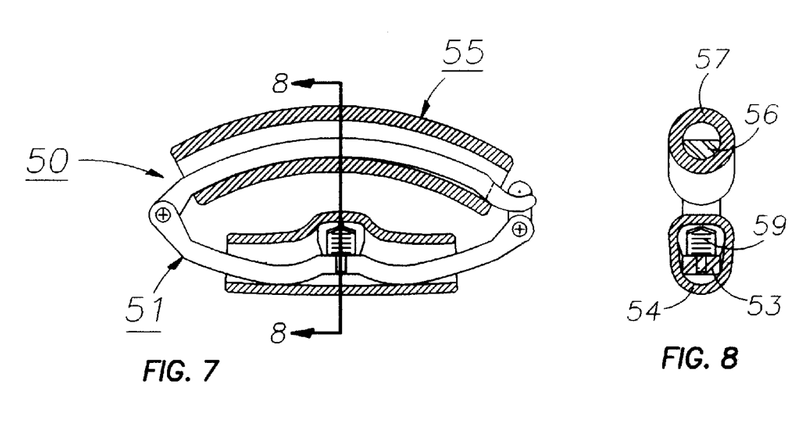
FIG. 7 is a front elevation view depicting an alternative embodiment of a clamp in accordance with the present invention.
FIG. 8 is a cross-section view taken along lines 8—8 in FIG. 7.
Figure 9:
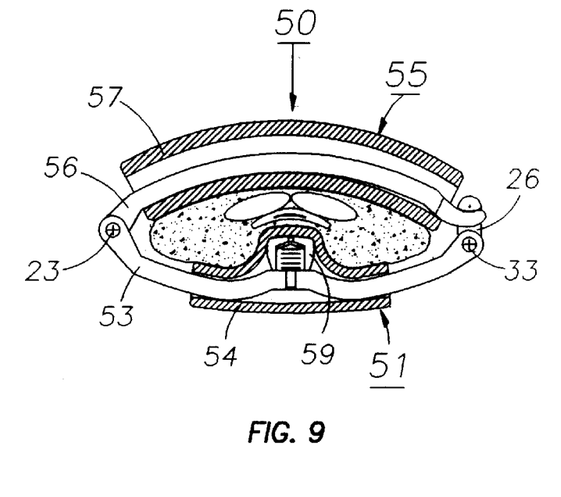
FIG. 9 is a transverse cross-section view of a penis showing the clamp of FIG. 7 closed or clamped about the penis and illustrating the compression by the closed clamp.
Figure 10:
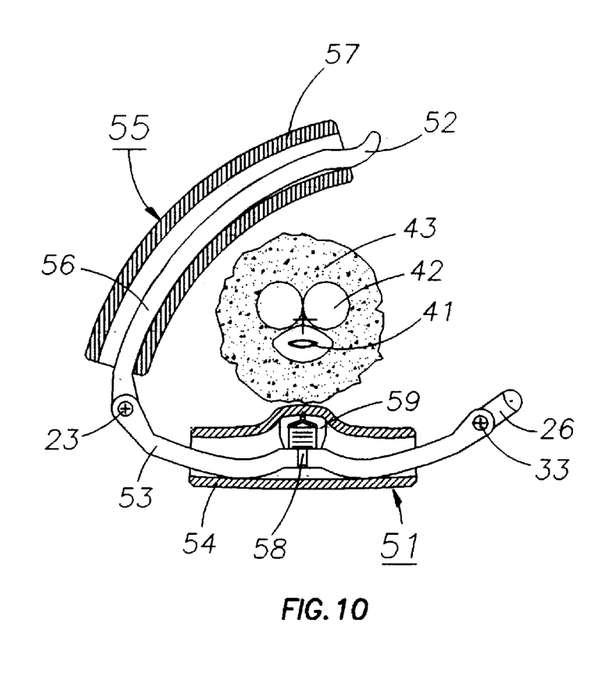
FIG. 10 depicts the clamp of FIG. 9 in the open position.

Latch assembly 25 is mounted similarly. See FIGS. 5 and 6. That is, a pivot pin 33 is mounted in the second end of one of the bows, illustratively the lower bow 11, at the slotted opening of hinge member 31, FIG. 5. Preferably, in this embodiment, the bifurcated, u-shaped hinge member 31 comprises extensions defining a slotted opening for receiving pivot pin 33. The pivot pin 33 is mounted in holes in the extensions of slotted end member 31, preferably in a removable friction fit, for receiving T-shaped latch member 26. A first or left end of the latch member 26 forms a hook 29, which snaps over pin 33. The second or right end of upper bow 16 is a bifurcated, u-shaped member 32 comprising extensions 34 defining a slotted opening for receiving the lateral upper crossbar or catch 28 of latch member 26 when the clamp is in the closed position. The catch 28 extends over the extensions of the latch member 32 in the upper bow 16 and secures the upper and lower bows in the closed condition shown in FIGS. 3 and 6. Preferably, the hook or latch 29 provides a secure but releasable friction fit over the pin 33. The hook opening faces outward when the clamp is closed and the latch is engaged in upper bow latch member 32, as shown in FIGS. 3, 5 and 6. When the latch member 26 is pivoted open as shown in FIG. 1, the opening faces downward, permitting easy removal of the friction fit latch for cleaning, replacement, etc.

Preferably, the clamp 10 is constructed of materials that can be sterilized if necessary in steam, ethylene oxide or boiling water without any damage to the assembly. In a presently preferred embodiment, the upper bow, the lower bow and the latch are made from polycarbonate plastic material, and the pins are grade 316 stainless steel.

b. Installation

Preferably, the penis is clean and dry prior to installing the clamp. A good practice is to lightly dust the penis shaft and testicles with baby powder or other suitable powder. Also, the clamp 10 should be clean and dry prior to installation. The clamp 10 is easy to install using both hands. It is installed horizontally across the penis with the latch side facing either left or right. The clamp is symmetrical and should be centered horizontally on the penis shaft centerline during installation. Using the hand that is most convenient, the head end of the penis is gripped, and the penis is pulled out perpendicular to the root, extending it to the limit. It is not necessary to hurt oneself in this process, just pull to reasonable limits of extension. While holding the penis shaft extended with one hand, the open clamp is picked up with the other hand and oriented so the arcuate projection 12 on the lower bow will be located on the bottom of the penis when the clamp is closed. Then one slides the open clamp over the penis shaft to approximately the center position along the shaft between the root and head. While holding the penis extended, the lower bow portion of the clamp is aligned horizontally, touching the bottom of the penis, and centered laterally (left to right) on the center of the penis, then the upper bow section is closed onto the lower bow section. While holding the aligned clamp closed about the penis using one hand, the head end of the penis is released from the other hand and the free hand is used to lift the latch into the slotted end of the upper bow. One may now release the clamp and allow it to hang free in the clamped position on the penis.

As shown in FIG. 3, the closely spaced bows of the closed clamp define a laterally elongated enclosure comprising a center region 37 flanked by side regions 35 and 36. The area of the enclosure is approximately equal to (or greater than) the cross-section area of the uncompressed penis 40. As is discussed at greater length below, the spacing between the closed bows and the area of the enclosure are easily changed by using latches of different lengths.

c. Operation

The shape of the bows and the center location of the projection 12 cause the projection to press against the lumen of urethra 41 upon installation and closure of the clamp and prevent lateral slippage of the clamp. The closure of the convex lower bow and the concave upper bow horizontally across the penis forces the lumen of urethra 41 to collapse into the corpus cavernosum 42 and musculus 43 of the penis, thereby stopping the free flow of urine through the penal urethra. However, as mentioned, the closed area of the oval enclosure is approximately equal to the cross sectional area of the penis shaft in its natural round, that is, its uncompressed shape. As a result, although closure of the clamp compresses the lumen urethra, preventing leakage, the mass of the musculus is shifted laterally into the side regions, allowing blood flow (circulation) to continue to the head end of the clamped penis.

Please note, although the lower bow is "convex" and the upper bow is "concave," this terminology is illustrative, not limiting. Other configurations can be used which comprise a short central region which compresses the penis and stops leakage, and adjacent spaces into which the compressed penis can expand to maintain blood circulation. For example, one bow could be convex and the other straight or nearly so, or both bows could be convex.

d. Pinch Adjustment/Latch Replacement

The clamp 10 is adjustable to facilitate larger and smaller penis shaft diameters and/or increasing or decreasing the magnitude of the compression or pinch pressure that is applied to the urethra when the clamp is closed. FIG. 3 shows the upper bow and lower bow together with the latch as one assembly. Adjustment of the pinch force is accomplished by changing the latch 26, to a longer or shorter latch (greater or smaller dimension d, FIG. 1), to thereby increase or decrease the distance between the upper bow and projection 12 when the clamp 10 is closed. The clamp 10 can be supplied as part of a kit containing several latches of different lengths and bows (at least upper bows) of different sizes, to accommodate penises of different cross-sectional areas (diameters) and/or to provide different pinch pressures. The pivot hole in the hook end of the latch member 26 can be slotted so as to provide a simple snap-on fit over the hinge pin 33. Removal of the latch 26 from the lower bow 11 is then accomplished by rotating the latch 26 downward until it stops at the bottom of the hinge slot. The latch rotation is continued with sufficient pressure to position the latch hard against the hinge slot bottom, causing the latch to lift off the hinge pin 33. Installing a new latch or replacing an old latch 26 is accomplished by locating the latch slotted hole (slot down) over the hinge pin 33 and pushing down firmly until the latch snaps over the hinge pin. It may be necessary to try several latches of different lengths in order to establish a comfortable tight fit of the clamp about the penis. The user may experiment with the location of the clamp along the penis shaft relative to the root/head position to find the most comfortable long term position.

In one example, using clamp components of the size depicted in FIGS. 1–6, a compression or pinch distance (the distance between the closed bows at their center) of 0.3" (inches) is provided by a latch 26 having "d" dimension 0.2". Of course, compression or pinch dimensions can be varied to accommodate penis shaft diameter, penis shaft muscle mass and bladder floor muscle control. The clamp 10 is readily adjusted for these factors using latches having different (smaller or larger) "d" dimensions and/or using bows (preferably upper bows 16) having center sections (17) of different configuration (shallower or deeper).

2. Alternative, Covered Tube Embodiment a. Design and Construction

FIGS. 7–10 depict an alternative clamp 50, in which the bows comprise frame members and tubular covers. Please note, components of clamp 50 which are the same as those of the clamp 10 are identified by the same reference numerals used for clamp 10. Components which are different are identified by reference numbers starting at 50. The covered tube embodiment 50 is similar to the integral bow embodiment described above, in that it comprises a lower bow 51 and an upper bow 55 which are pivotally joined by pins 23 and 33. The lower bow 51 comprises a frame member 53 fitted with a tube or cover 54 of material such as latex or silicon rubber. Similarly, the upper bow 55 comprises a frame member 56 fitted with a tube or cover 57 of material such as latex or silicon rubber. Lower bow 51 pivotally mounts latch member 26 at the hinge point defined by the pin 33. The pivotal latch is captured by slotted end section of upper bow 55. Lower bow 51 is fitted with a threaded stud 58 that receives a pinch plug 59. Lower bow 51, upper bow 55, latch member 26, stud 58 and pinch plug 59 preferably are made from easily cleanable, yet durable, relatively rigid, yet flexible material such as plastic. In a preferred embodiment, the upper bow frame member, lower bow frame member, latch, stud and pinch plug are polycarbonate plastic and the pins are grade 316 stainless steel. The tube covers are medical grade latex or silicon tubing.

The installation, operation and function are the same as for the preferred, integral bow design.

b. Adjustments

The clamp or clamp 50 is adjustable to facilitate increasing or decreasing the amount of pinch pressure that is applied to the urethra when the clamp is closed and latched. Referring again to FIGS. 7–10, stud 58 and pinch plug 59 comprise one assembly. Stud 58 is threaded and cemented into lower bow member 53. Pinch plug 59 is threaded to match the threaded stud. The pinch plug is threaded over the stud and is positioned for acceptable urethra pinch pressure. This adjustment can be made by the user at any time by moving the latex or silicon tubing 54 laterally free of the pinch plug 59. The pinch plug can then be rotated on the threaded stud as necessary to move the pinch plug up or down to add or relieve urethra pinch pressure. This adjustment should be made in small increments, for example, ¼ turns up or down. After adjusting the pinch plug, one slides the latex or silicon tubing back over the pinch plug and stud assembly, and re-installs the clamp on the penis and checks for improved fit and pressure conditions. The user should experiment with the location of the clamp along the penis shaft relative to the root/head position to find the most comfortable long term position.

The compression or pinch dimensions of clamp 50, FIGS. 7–10 can be varied to accommodate penis shaft diameter, penis shaft muscle mass and bladder floor muscle control, by using latches of different lengths and/or by using bows of different configurations, both as described above relative to clamp 10, FIGS. 1–6, and/or by adjusting the pinch plug positioning, as described immediately above.

3. Adjustable Spacing Embodiment a. Design and Construction

FIGS. 11–15 depict a presently preferred embodiment 70 of an adjustable male incontinence clamp which embodies the present invention. The operation of clamp 70 is similar to that of clamp 10, FIGS. 1–6. Several components are modified to make the clamp 70 adjustable, meaning the spacing between the upper and lower bows can be changed without removing and replacing components. The modified components of clamp 70 are designated by reference numbers 7x, 8x and 9x, in place of the designations 1x, 2x and 3x used for clamp 10. Please note, the components 7x, 8x, 9x do not always correspond to those designated 1x, 2x or 3x. For example, bore 81 has no equivalent 21.

Figure 4:
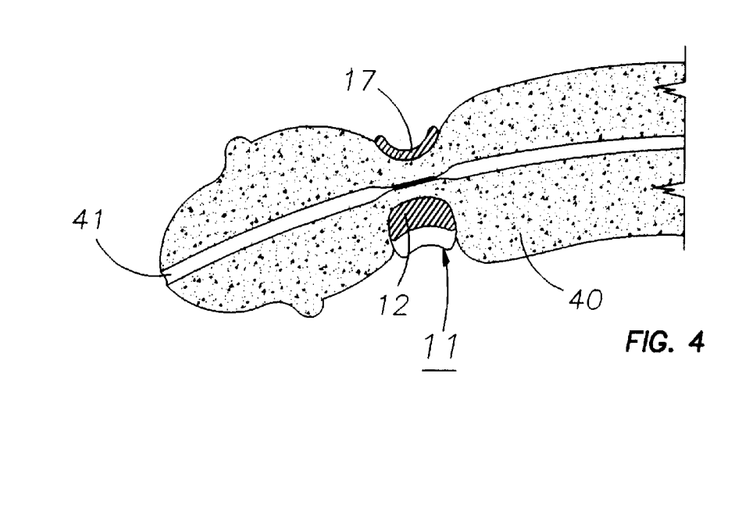
FIG. 4 is a longitudinal cross-section view of the penis of FIG. 3 taken along the direction of line 4—4 in FIG. 3, illustrating the longitudinal position and the compression action of the clamp.
Figure 13:
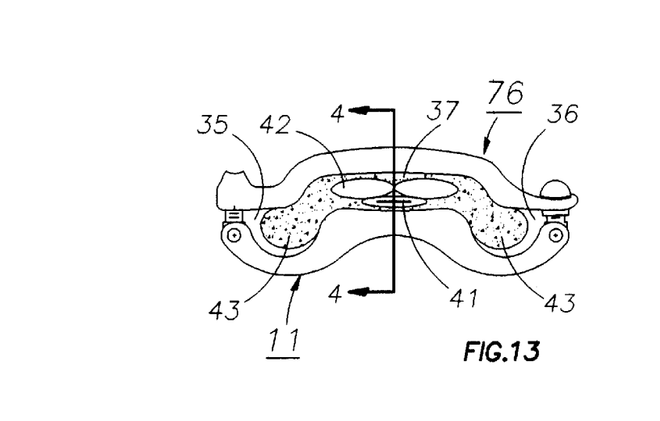
FIG. 13 is a transverse cross-sectional view of a penis showing the clamp of FIG. 11 closed or clamped and illustrating the compression by the closed clamp.

The clamp 70 comprises a lower bow-shaped member or bow 11 and an upper bow-shaped member or bow 76. The two bows are pivotally joined at one end (illustratively the left end) by pivotal hinge assembly or pivot 80, which includes threaded eye stud 83, and are latched in releasable fashion at the opposite end (right end) by latch assembly 85, which includes latch 84. As explained in detail below, and as is shown in FIGS. 4 and 13, when the clamp 70 is closed about the penis, the bows compress the penis in such a way that leakage is prevented, yet blood circulation is maintained to the clamped head end of the penis.

Figure 11:
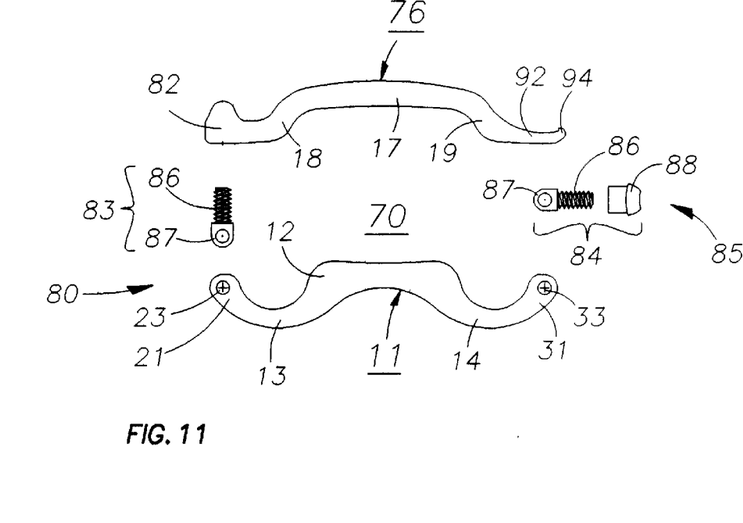
FIG. 11 is an exploded front elevation view depicting yet another embodiment of a clamp in accordance with the present invention.
Figure 14:
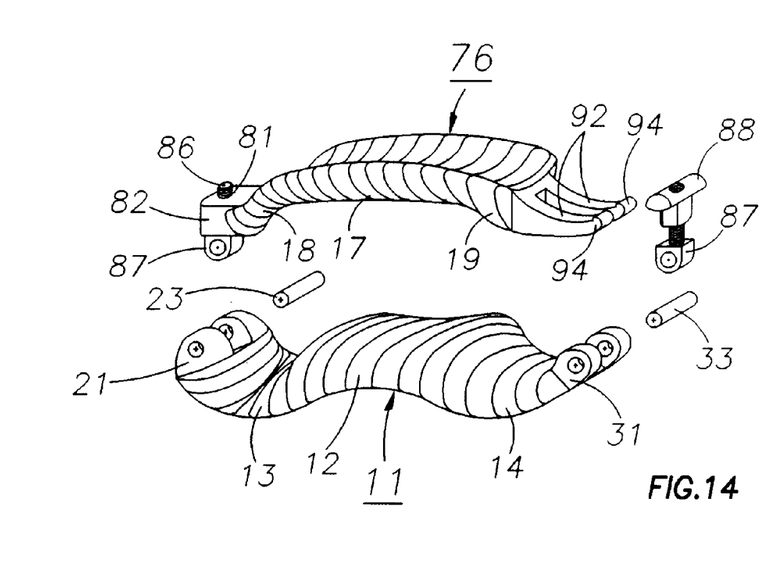
FIG. 14 is an isometric exploded view of the parts forming the clamp assembly shown in FIGS. 11–13.
Figure 15:
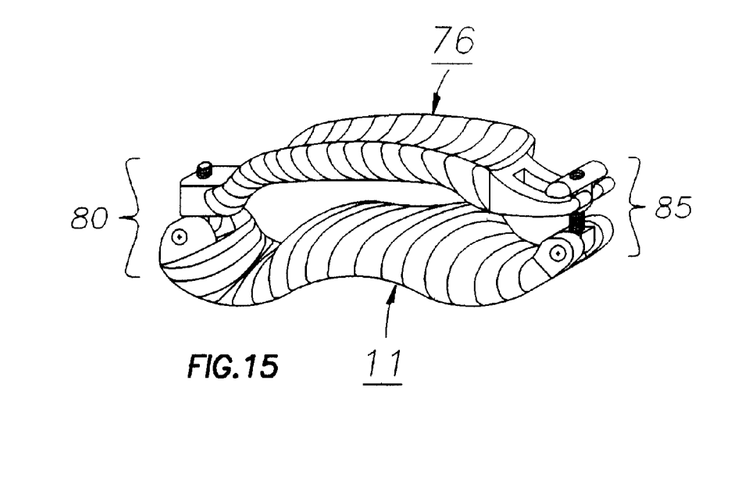
FIG. 15 is an isometric view of the clamp assembly shown in FIG. 13.

Referring in particular to FIGS. 11, 14 and 15, the hinge assembly 80 comprises the slotted end section hinge member 21 of lower bow 11; the pivot pin 23 which also defines pivot 23; end section hinge member 82 of upper bow 76; and the threaded eye stud 83. The eye stud 83 comprises a base or eye 87 having a throughhole, and a threaded stud 86. Pivot pin 23 is mounted in a hole in the slotted hinge member 21, preferably via a friction fit which permits removal of the pin. The stud eye 87 is pivotally mounted on the pivot pin 23. A threaded bore 81, FIG. 14, in the upper bow hinge member 82 receives mating threaded stud 86. Eye stud 83 provides vertical adjustment of the spacing between upper bow 76 and lower bow 11 at the first, pivot end of the clamp 70, FIG. 11. Pivot pin 23 can be removed from lower bow 11 for repair, replacement, cleaning, etc., of the pin 23, the bows, and the associated components by applying lateral pressure to pin 23 using a blunt round object of lesser diameter than pin 23.

Referring further to FIGS. 11, 14 and 15, the latch assembly 85 comprises the slotted end section hinge member 31 of lower bow 11; pivot pin 33 which also defines pivot 33; slotted latch end section 92 of upper bow 76; and latch 84. The latch 84 comprises base or eye 87 having a throughhole, threaded stud 86; and a threaded tee nut 88 which can be screwed onto the stud 86 and comprises lateral extensions for latching onto the upper bow. The pivot pin 33 is mounted in a hole in the slotted hinge member 31, preferably via a friction fit which permits removal of the pin. The stud eye 87 is pivotally mounted on the pin/pivot 33. The open ends of slotted member 92 have projections 94 (see FIG. 14) that form a buttress. When the latch 84 is pivoted closed onto the slotted member 92, the lateral extensions of the tee nut 88 extend over the slotted member and are seated against the buttress projections 94, preventing the tee nut from sliding out of engagement with slotted member 92 and securing the upper and lower bows in the closed condition shown in FIGS. 11, 14 and 15. Pivot pin 33 preferably is a friction fit and can be removed from lower bow 11, permitting removal of the bows and the other components in addition to the pin 33, for repair, replacement, cleaning, etc. This is done by applying lateral pressure to pin 33 using a blunt round object of lesser diameter than pin 33.

As discussed regarding the embodiment 10, for convenience I refer to the lower bow 11 as being convex and the upper bow 76 as being concave. The two bows have mating, vertically short unshaped configurations. Preferably each bow is a relatively rigid, yet resilient single piece member formed of material such as plastic. The lower bow 11 comprises an upward-extending (inward-extending) center section or projection 12 flanked by opposite side sections 13 and 14. Projection 12 has a slight depression at approximately its center, which helps in positioning and mounting the clamp 70 on the shaft of a penis. Projection 12 and mating side sections 13 and 14 on bow 11, have blended radii and are highly polished to prevent irritation when closed on the penis shaft. The upper bow 76 comprises an upward-extending (outward-extending) center section 17 flanked by opposite side sections 18 and 19. Projection 17 and mating side sections 18 and 19 on bow 16, have blended radii and are highly polished to prevent irritation when closed on the penis shaft.

Although it is preferred that both the hinge and the latch be adjustable and adjusted, the clamp will work with only one being adjustable, or with only one being adjusted.

b. Installation, Operation, Adjustment

Figure 12:
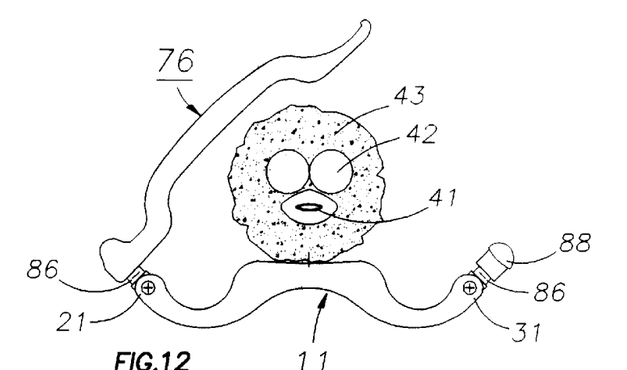
FIG. 12 depicts a transverse cross-sectional view of a penis about which the clamp of FIG. 11 is horizontally centered in an open orientation, prior to closure.

As shown in FIG. 13, the closely spaced bows of the closed clamp define a laterally elongated enclosure comprising a center region 37 flanked by side regions 35 and 36. The area of the enclosure is approximately equal to (or greater than) the cross-section area of the uncompressed penis 40. The spacing between the closed bows and the area of the enclosure are easily changed by using the threaded eye stud adjustments provided at the first and second pivot ends of the clamp. That is, the spacing between the upper and lower bows at the latch (right) end can be adjusted by simply rotating the tee nut 88 in opposite directions on the stud to decrease or increase the spacing. The spacing between the upper and lower bows at the hinge (left) end is adjusted, that is, decreased or increased, by rotating the stud 86 in opposite directions within hinge member 82, or vice versa. For example, with the latch (right) end unlatched, as shown in FIG. 12, the spacing at the pivot (left) end can be decreased or increased by rotating the upper bow 76 around the stud 86 without removing the threaded eye stud 83 from the clamp.

Adjustment of the clamp 70 as described above accommodates larger and smaller penis shaft diameters and/or increasing or decreasing the magnitude of the compression or pinch pressure that is applied to the urethra when the clamp is closed. FIG. 13 shows the upper bow and lower bow together with the latch as one assembly. The clamp 70 provides for quick easy pinch pressure changes by increasing or decreasing the distance between the upper bow 76 and projection 12 on the lower bow 11 when clamp 70 is closed. Pinch adjustments can be made at any time as the need may arise. Ideally, a good practice is to maintain a near parallel alignment of upper and lower bow sections during pinch pressure adjustments. It may be necessary for several pinch adjustments to be made by the new user for initial comfortable fit. The threaded eye studs at the clamp ends make this primary pinch fit quick and easy for the user and, also provide quick easy minor pinch adjustments during the wearing cycle. The user may experiment with the clamp location along the penis shaft relative to the root/head position to find the most comfortable long term position.

c. Example

In one example, clamp components as depicted in FIGS. 11–15 provide 0.187" inches of parallel pinch adjustment.

Minimum pinch opening, FIG. 13, is 0.187" inches as measured between upper bow 76 and the projection 12 of lower bow 11, with a maximum pinch opening at 0.375" inches. Threaded eye stud screw threads are NC 5–40 which provides 0.025" inch adjustment per revolution and 0.0125" inch adjustment per ½ revolution. Variable compression or pinch dimensions accommodate various penis shaft diameters, penis muscle mass and the degree of effective natural bladder floor muscle control. Clamp 70 as provided with threaded screw adjustments provides all the mechanics to establish a quick comfortable fit together with complete freedom of anytime, anyplace adjustment.

In the various embodiments and aspects described here, the clamp according to the present invention provides an easy means of support, is easy to install on the penis shaft, and can be adjusted with relative ease to fit a wide range of penis shaft diameters. The clamp can be worn with very little discomfort for extended periods of time, and is quickly opened when the urge to urinate is apparent and quickly closed when the bladder is empty.

The present invention has been described in terms of preferred and other embodiments. The invention, however, is not limited to the embodiments described and depicted. Rather, the invention is limited only by the appended claims and equivalents thereof

What is claimed is:

1. A clamp for closing about a penis and stopping penile leakage, comprising a generally concave first bow having first and second ends; a generally convex second bow having first and second ends and an upward-extending center section having a substantially flat upper surface comprising a depression therein; each of the upper and lower bows being rigid yet flexible and comprising plastic; an adjustable hinge pivotally joining the bows at the first ends thereof, and an adjustable releasable latch holding the closed bows together at the second ends thereof; the adjustable hinge and latch holding the closed upper and lower bows spaced apart at a first adjustable distance at approximately a center region of the bows and a second adjustable distance at side regions on opposite sides of the center, for securely positioning and compressing the penis between the first and second bows along the center section of the second bow without discomfort and to close the urethra, while allowing the penis to expand into the side regions to maintain blood circulation.

2. A method for stopping penile leakage, comprising providing a clamp having upper and lower bows; positioning the clamp transversely across the shaft of a penis; and closing the bows to provide a first, relatively small substantially uniform center section spacing therebetween proximate the cross-sectional center of the penis shaft and a second, relatively larger spacing therebetween on opposite sides of the penis shaft; the first spacing closing the lumen of urethra and suppressing liquid flow through the lumen of urethra, and the second spacing allowing sideways displacement of the penis musculus to maintain blood circulation to the penis head.

3. A clamp for closing about a penis and stopping penile leakage, comprising: a generally convex lower bow having first and second ends; a generally concave upper bow having first and second ends; a pivot or hinge comprising a threaded eye stud having length and having the eye section thereof mounted to the first end of one of the upper and lower bows and being threaded along the length thereof into the first end of the other of the two bows; a latch comprising a threaded eye stud having length and a threaded tee mounted along the length of the threaded eye stud; the eye section of the latch being pivotally mounted to the second end of one of the upper and lower bows and the tee being captured by the second end of the other of the two bows; the pivot and latch holding the upper and lower bows closed and spaced apart a first distance at approximately the center of the bows and a second distance on the sides of the center, for compressing the penis at the center to close the urethra, while allowing the penis to expand into the side regions to maintain blood circulation; and at least the first distance being determined by the extent to which the length of the threaded eye stud of the pivot is threaded into the first end of the one bow and by the position of the tee along the length of the threaded eye stud of the latch.

4. The clamp of claim 3, wherein each of the upper and lower bows is an integral member of rigid, yet flexible material.

* * * * *